United States Patent [19]

Brunty et al.

[11] Patent Number: 6,131,460
[45] Date of Patent: *Oct. 17, 2000

[54] ULTRASONIC INSPECTION SYSTEM FOR LAMINATED STIFFENERS

[75] Inventors: Troy W. Brunty, Perry, Utah; Fred D. Young, Bellevue, Wash.

[73] Assignee: The Boeing Company, Seattle, Wash.

[ * ] Notice: This patent is subject to a terminal disclaimer.

[21] Appl. No.: 09/250,042

[22] Filed: Feb. 12, 1999

Related U.S. Application Data

[60] Division of application No. 08/829,968, Apr. 1, 1997, which is a continuation-in-part of application No. 08/664,899, Jun. 17, 1996, abandoned, which is a continuation-in-part of application No. 08/086,283, Jul. 1, 1993, Pat. No. 5,585,564.

[51] Int. Cl.$^7$ .................................................. G01N 29/04
[52] U.S. Cl. .................................. 73/634; 73/641; 73/636
[58] Field of Search ............................. 73/634, 636, 635, 73/628, 632, 633, 640, 641, 588, 598, 600, 618, 620, 866.5

[56] References Cited

U.S. PATENT DOCUMENTS

| 3,121,324 | 2/1964 | Cowan | 73/67.5 |
|---|---|---|---|
| 3,129,581 | 4/1964 | Bande | 73/67.8 |
| 3,224,254 | 12/1965 | Loving | 73/71.5 |
| 3,375,706 | 4/1968 | Pandelis et al. | 73/67.9 |
| 3,552,190 | 1/1971 | Lefebvre | 73/67.7 |
| 4,114,456 | 9/1978 | Dory | 73/622 |
| 4,719,808 | 1/1988 | Baumann et al. | 73/622 |
| 4,848,159 | 7/1989 | Kennedy et al. | 73/641 |
| 5,031,458 | 7/1991 | Young et al. | 73/636 |
| 5,585,564 | 12/1996 | Brunty et al. | 73/634 |

FOREIGN PATENT DOCUMENTS 2064 773  12/1979  United Kingdom .

Primary Examiner—Helen C. Kwok
Attorney, Agent, or Firm—Conrad O. Gardner

[57] ABSTRACT

An ultrasonic one pass inspection system for determining the presence, location, and size of flaws in laminated structure such as an "I" stiffener in a single inspection cycle. The exemplary system includes an immersion tank, six (6) single probes, 184 transducers, four (4) motor assemblies, two (2) encoder assemblies, a collection tank, and a recirculation assembly. The probes are designed to match the shape of the stiffener. Two (2) motors fore and two (2) motors aft of the immersion tank, produce information related to the position of the stiffener with respect to the position of the transducer. The position encoder is spring-loaded against the stiffener.

1 Claim, 14 Drawing Sheets

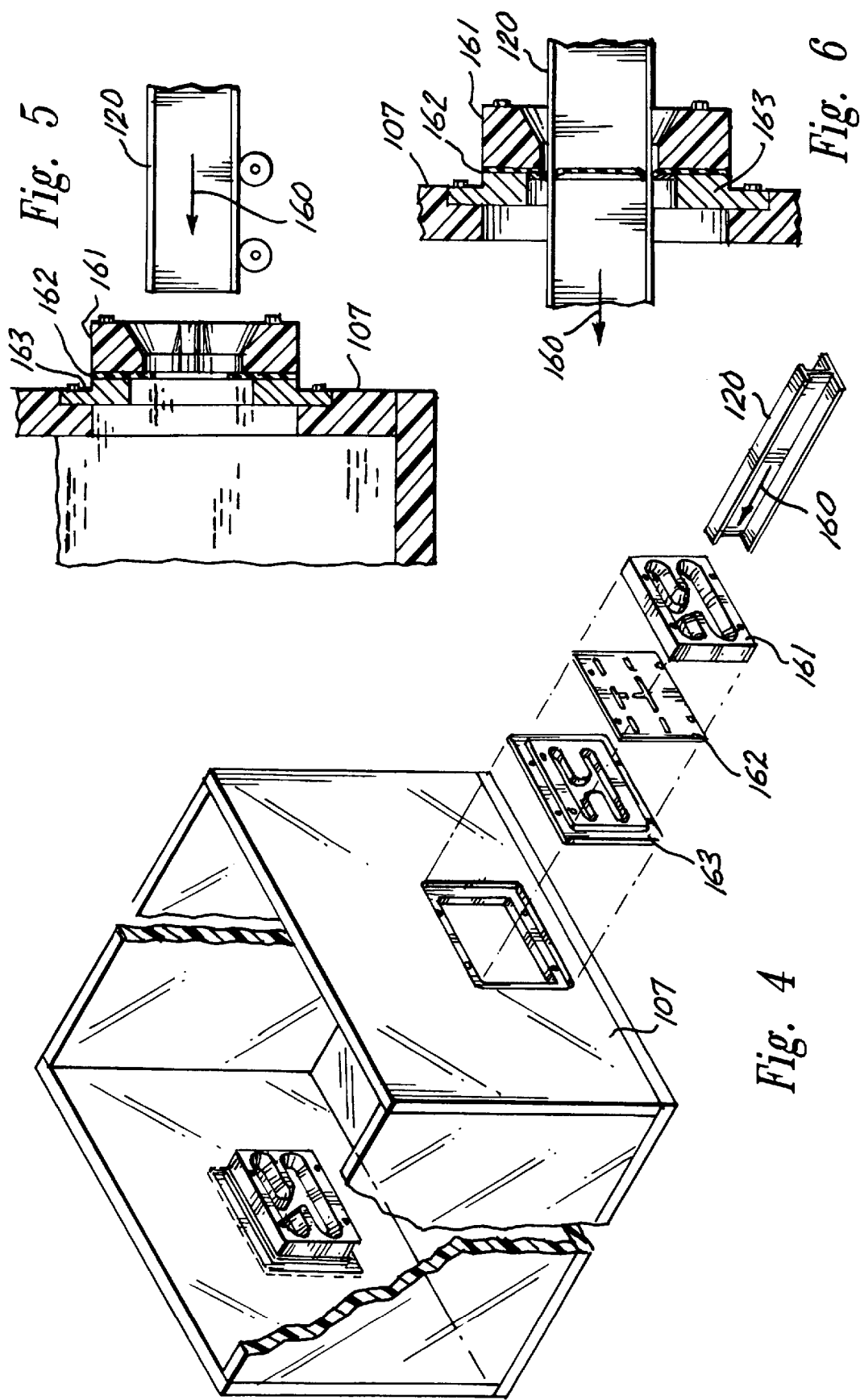

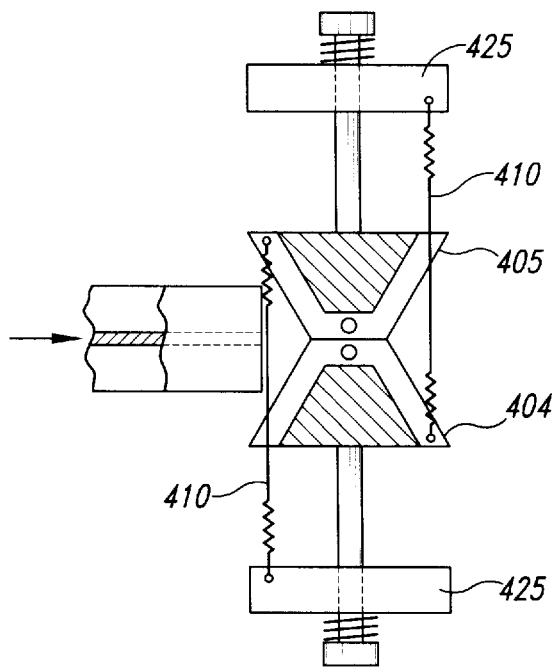 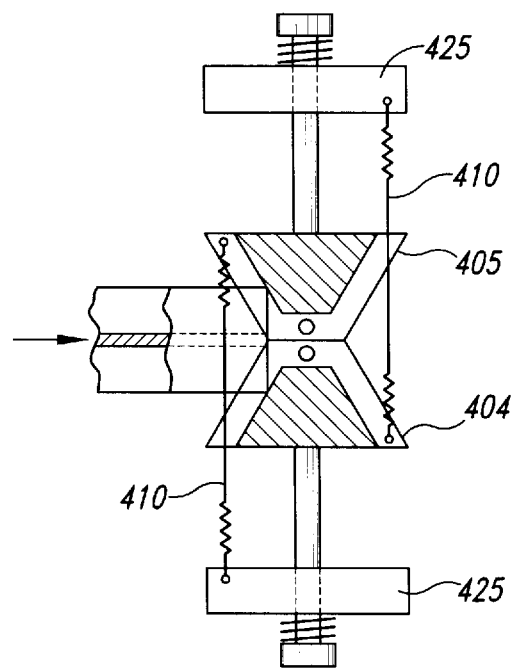
*Fig. 15*     *Fig. 16*
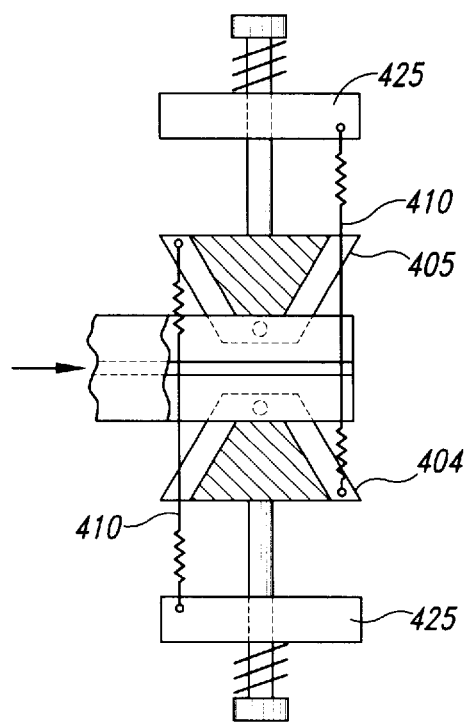
*Fig. 17*

ULTRASONIC INSPECTION SYSTEM FOR LAMINATED STIFFENERS

RELATED PATENT APPLICATIONS

This is divisional application to continuation-in-part U.S. patent application Ser. No. 08/829,968, filed Apr. 1, 1997, assigned to The Boeing Company, which is continuation-in-part of U.S. patent application Ser. No. 08/664,899, filed Jun. 17, 1996, now abandoned assigned to The Boeing Company, which is a continuation in part of U.S. patent application Ser. No. 08/086,283, filed Jul. 1, 1993, now U.S. Pat. No. 5,585,564, issued Dec. 17, 1996, assigned to the Boeing Company

FIELD OF THE INVENTION

The present invention relates to ultrasonic inspection and, more particularly, to the use of ultrasonic transducers to detect and size flaws in laminated composite "I" stiffeners.

BACKGROUND OF THE INVENTION

The use of graphite/epoxy materials for building aircraft structures is expanding. For example, graphite/epoxy "I" stiffeners are +being used to give strength and rigidity to the empennage of new aircraft. In order to keep pace with this expanding use of these new materials, new and faster methods for inspection are required.

In general, ultrasonic systems, whether multiple or single channel (a pair of transducers, transmitting and receiving) requires repeated passes over the part for 100% ultrasonic inspection of the part. This is a time consuming procedure.

The present invention, hereinafter described "feedthrough stiffener inspection system" (FSIS), provides a rapid ultrasonic inspection of the aforementioned "I"-shaped stiffeners. FSIS is a one pass, 100% inspection capable of handling stiffeners, regardless of length. FSIS's transducers are stationary, which eliminates the need for long cables (a problem characteristic of devices which creep along the stiffener while inspecting or gantry-type robots). Also, because FSIS is stationary, one person can control movement of the part through the system and evaluate the inspection data at the same time. Because FSIS is an immersion ultrasonic technique, its transducer shoes are much more simple and cost effective to design and manufacture than those of other inspections which are relegated to using a bubbler technique. Compared to other immersion techniques, FSIS is a faster technique. Due to its small size, FSIS does not require a large storage area while not in use.

In accordance with the present invention, there is provided a feedthrough stiffener inspection system for determining the presence, location, and size of flaws in the radius region and adjacent areas of a structure. A preferred embodiment of the present system comprises: 6 probes with a plurality of transducers; an immersion tank with "I"-shaped windows fore and aft; a water collection tank; a fore and aft motor drive assembly; a fore and aft position encoder assembly; a water recirculation system; and, a plurality of roller tables.

In accordance with further features of the present invention, the probe assembly further comprises a plurality of individual shoes configured for complementary engagement with the structure under inspection. The individual shoes are pushed toward each other by spring assemblies so as to clamp the "I" stiffener. The plurality of transducers inspect the "I" stiffener and produce relevant inspection information.

In accordance with further features of the present invention, the fore and aft motor assemblies are mounted to a spring-loaded platform which pushes the motor assemblies against the "I" stiffener. A pressure wheel with movable platform is directly opposite the motor drive wheel. The interaction of the two wheels create the translational movement of the "I" stiffener enabling it movement through the immersion system. The fore and aft motor assemblies operate synchronously.

In accordance with yet further features of the present invention, the position encoder assemblies are mounted to a spring-loaded platform. The relative motion of the structure moving through the system drives the encoder, thereby producing position information for generating C-scans. The fore and aft position encoder assemblies operate synchronously. As the structure moves through the system, the fore encoder electronics is activated. When the structure disengages from the fore position encoder, the aft encoder is activated until the structure disengages from the aft encoder.

In accordance with still further features of the present invention, the recirculation system maintains the water level of the immersion tank so that the "I" stiffener and probes are always immersed. The recirculation system recycles the water from the collection tank back into the immersion tank.

In accordance with yet further features of the present invention, conveyor tables fore and aft of the immersion system support the structure as it moves through the inspection station.

BRIEF DESCRIPTION OF THE DRAWINGS

The foregoing and other features and advantages of the invention will become more readily appreciated as the same becomes further understood by reference to the following detailed description when taken in conjunction with the accompanying drawings, wherein:

FIG. 4 is an exploded isometric view illustrating the stiffener and immersion tank;

FIG. 5 is a side view illustrating the stiffener before entering the immersion tank;

FIG. 6 is a side view illustrating the stiffener in the immersion tank;

Figure 7:
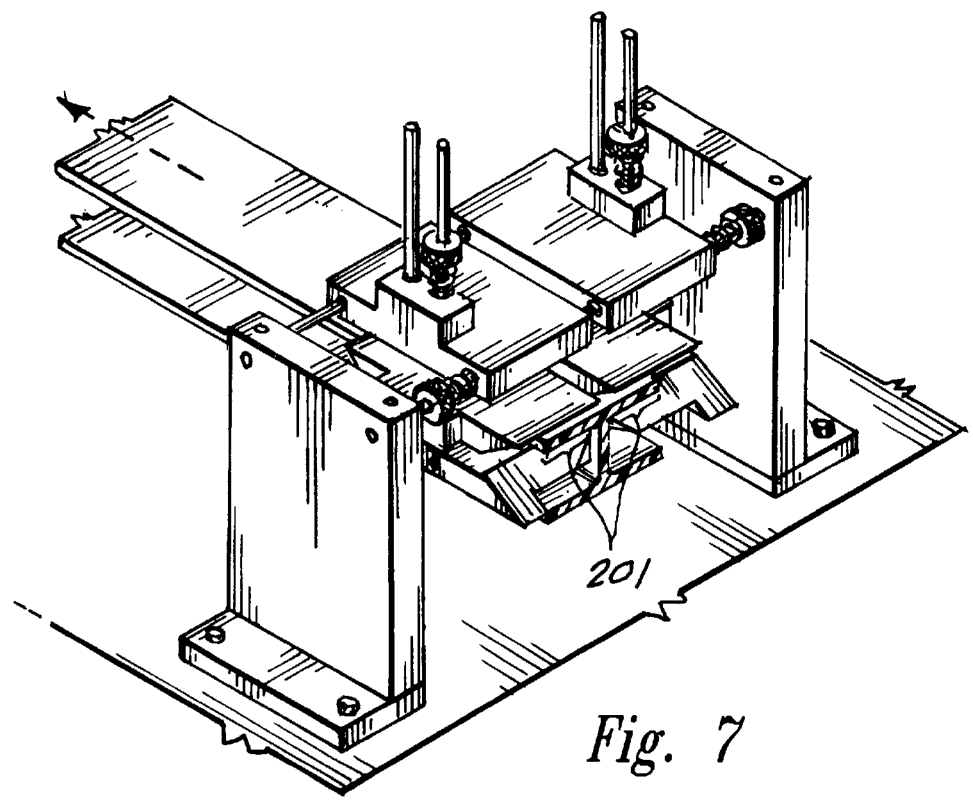
FIG. 7 is an isometric view of the cap probe.
Figure 7A:
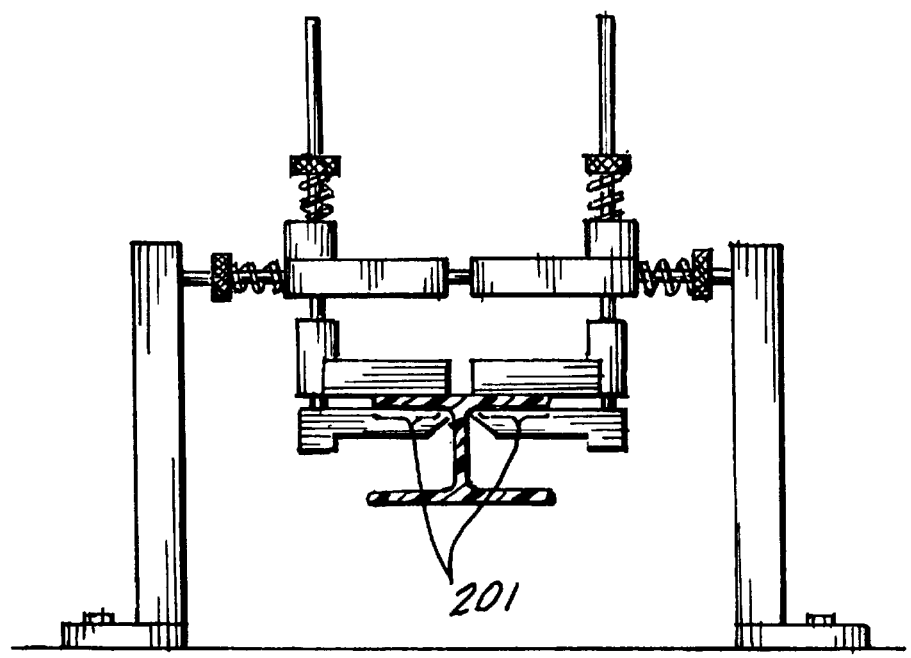
Figure 8:
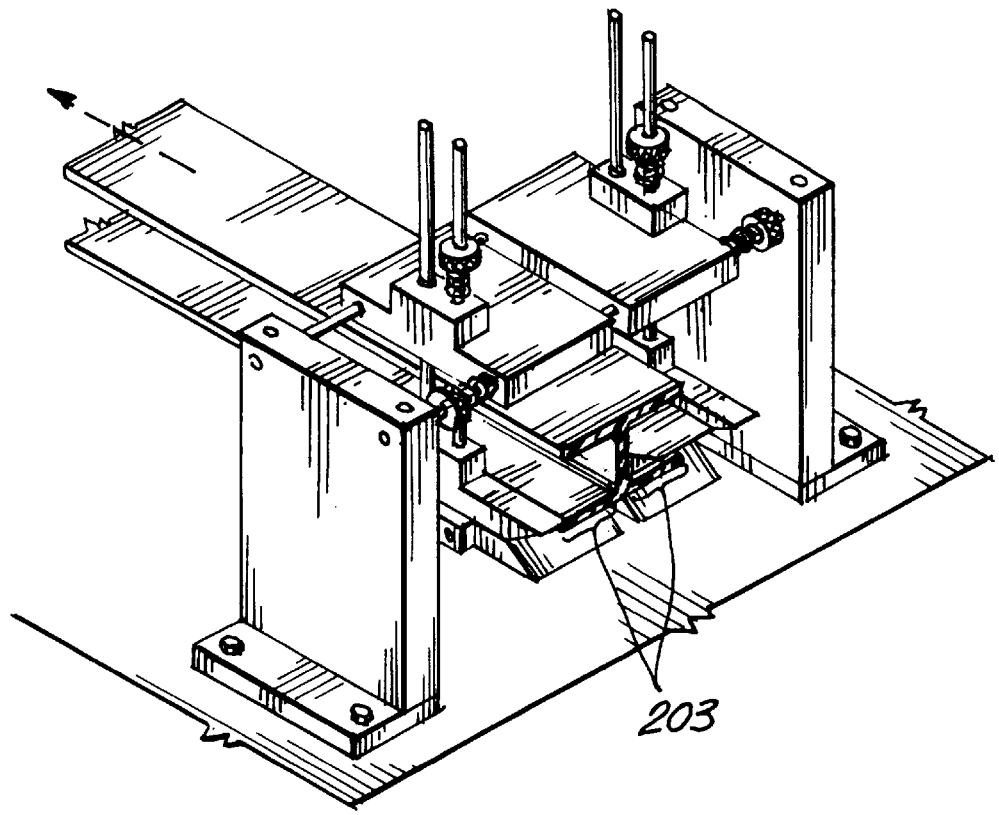
Figure 8A:
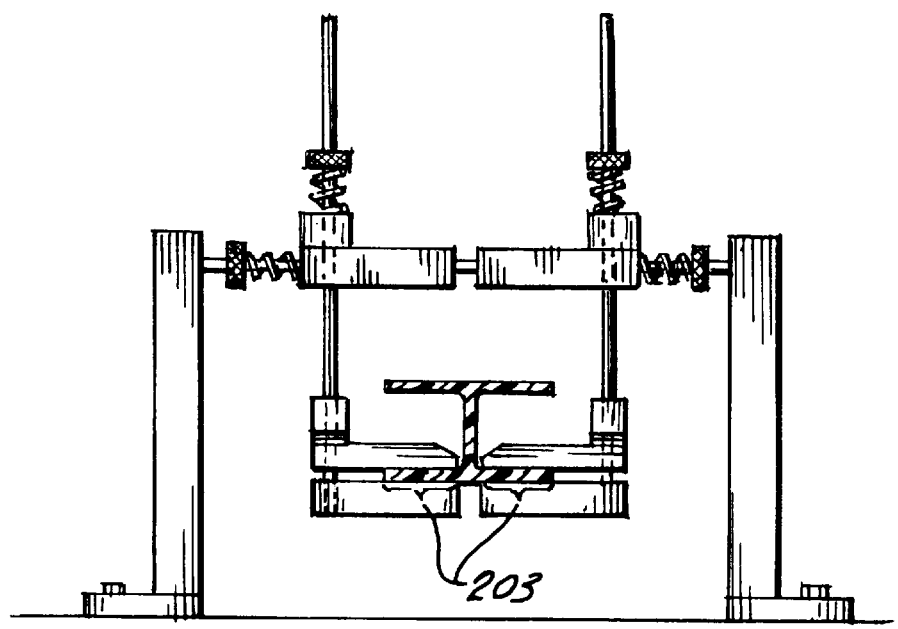
Figure 9:
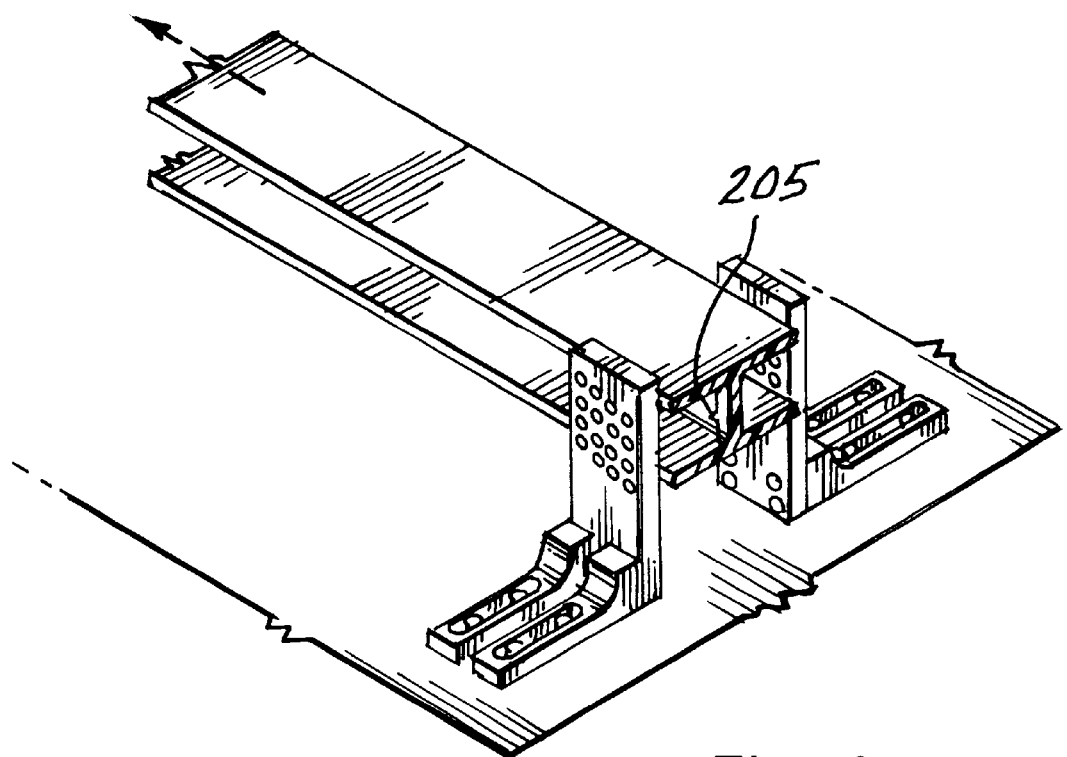
Figure 9A:
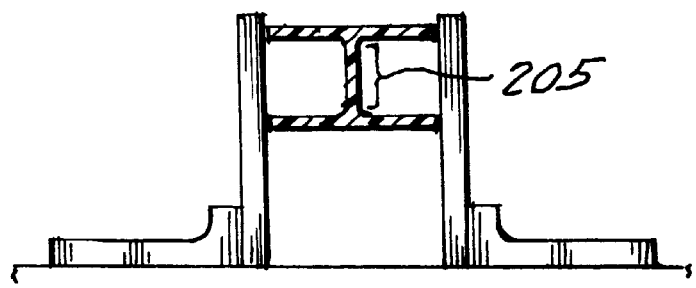
Figure 10:
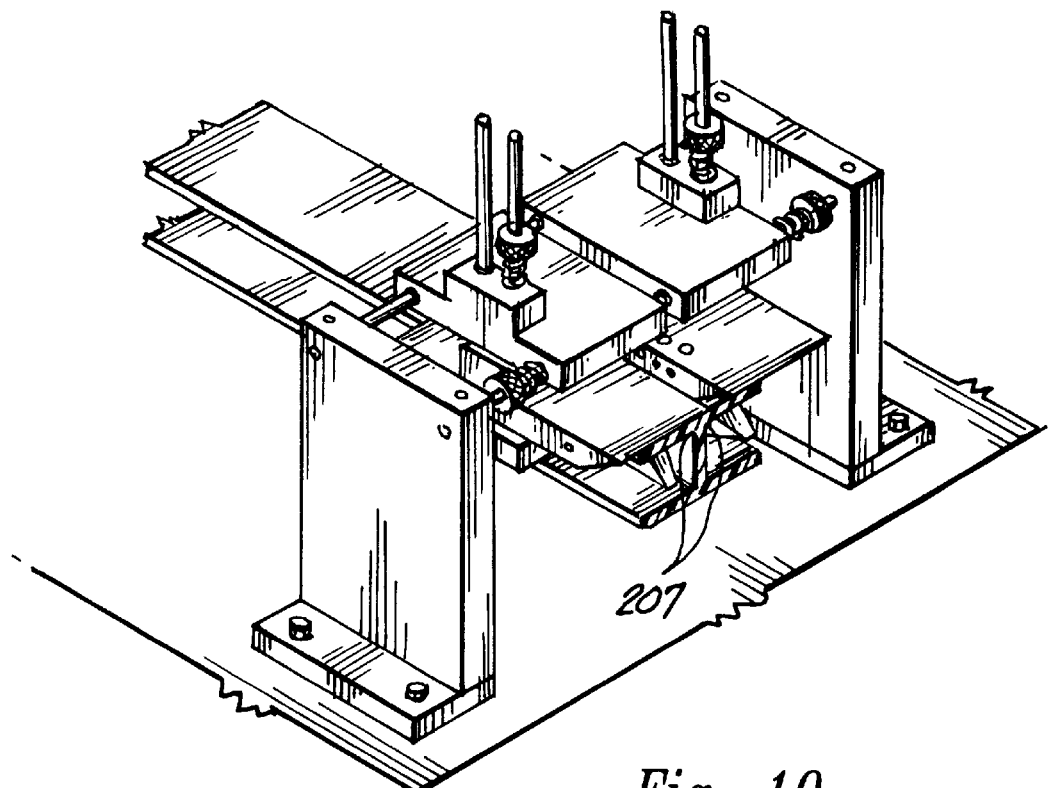
Figure 10A:
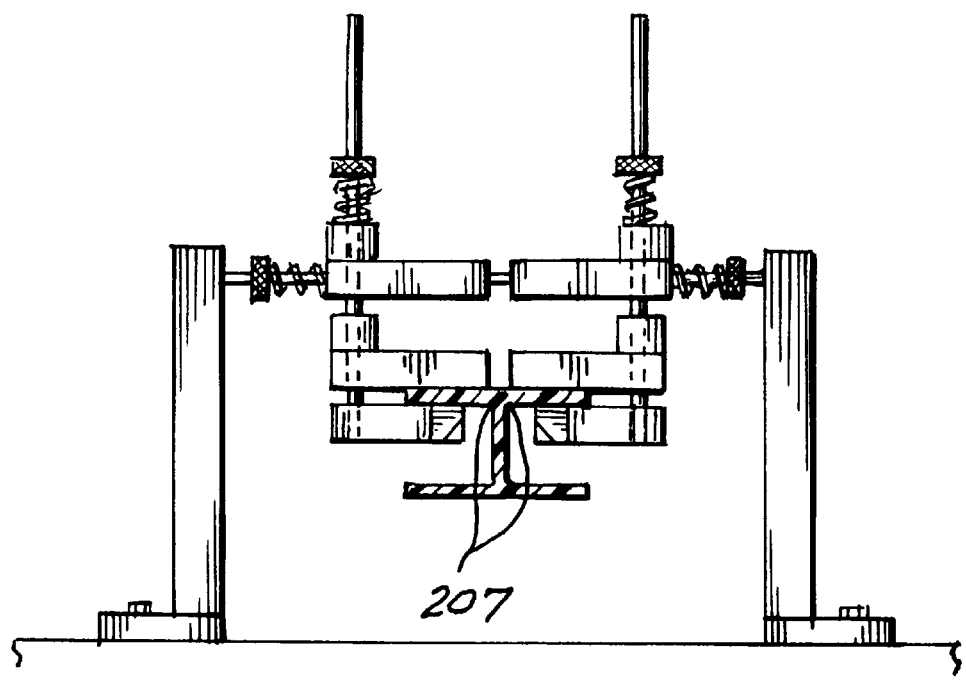
Figure 11:
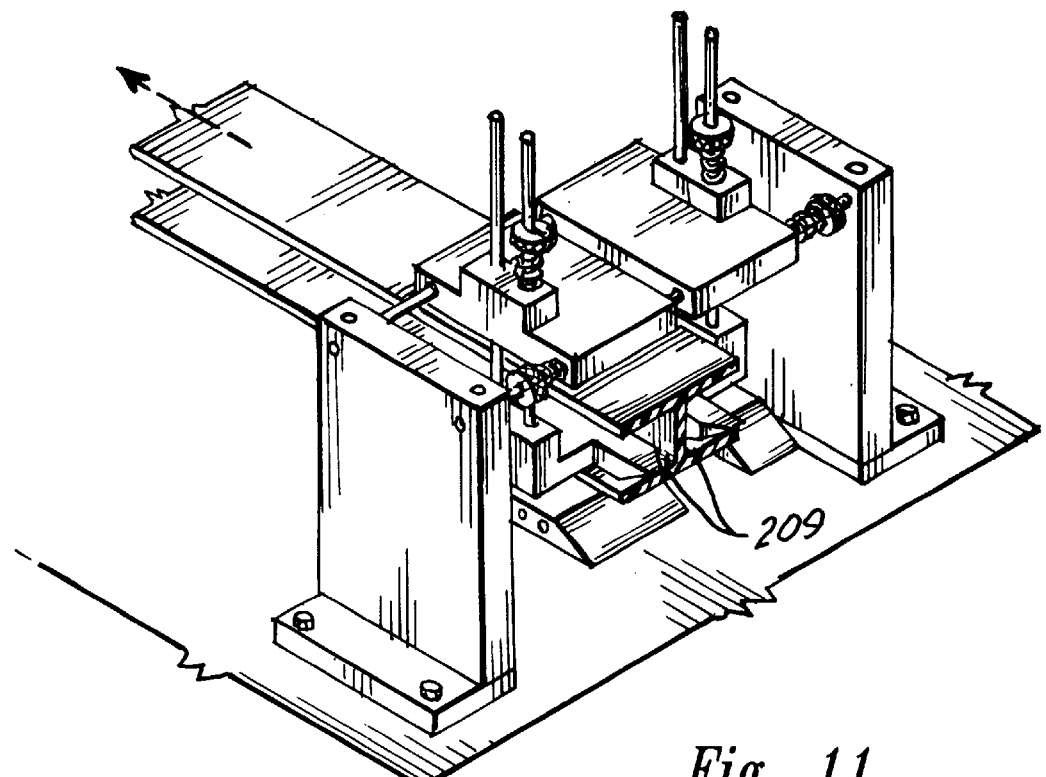
Figure 11A:
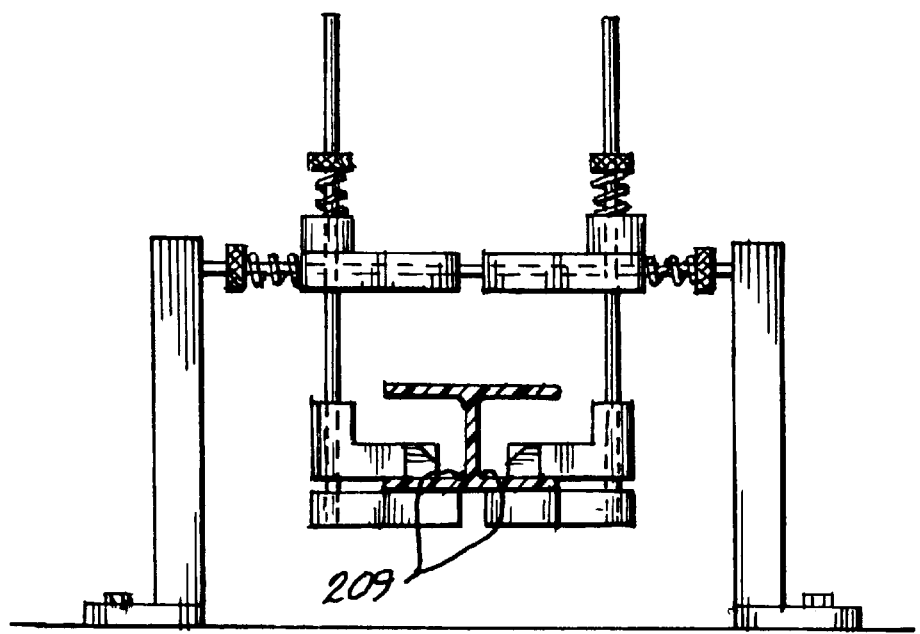
Figure 12:
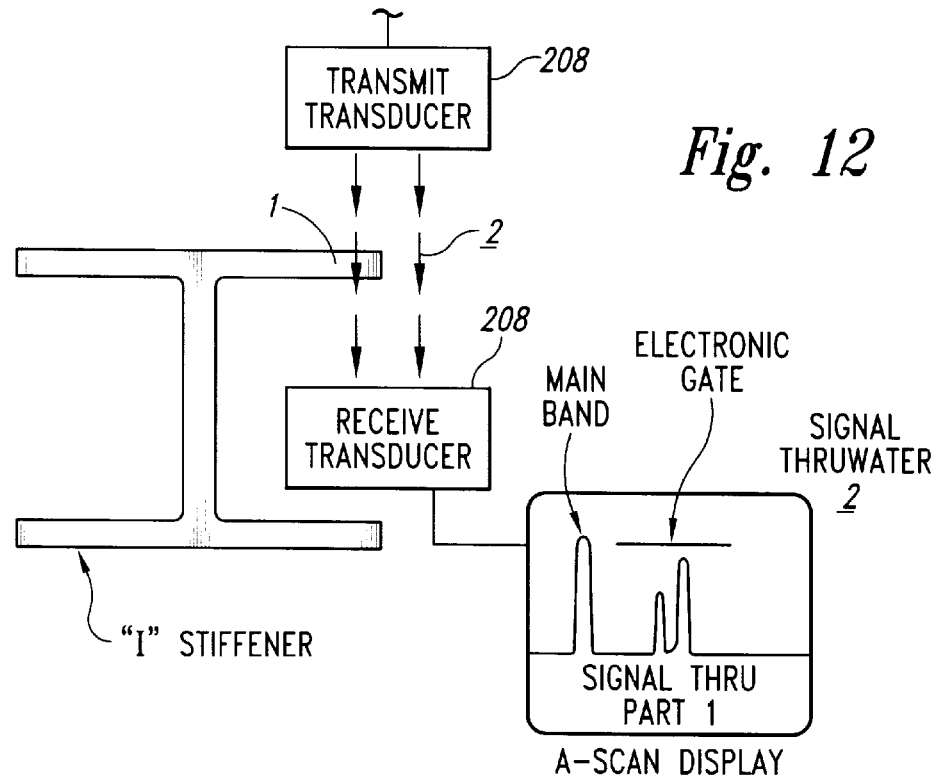
Figure 12A:
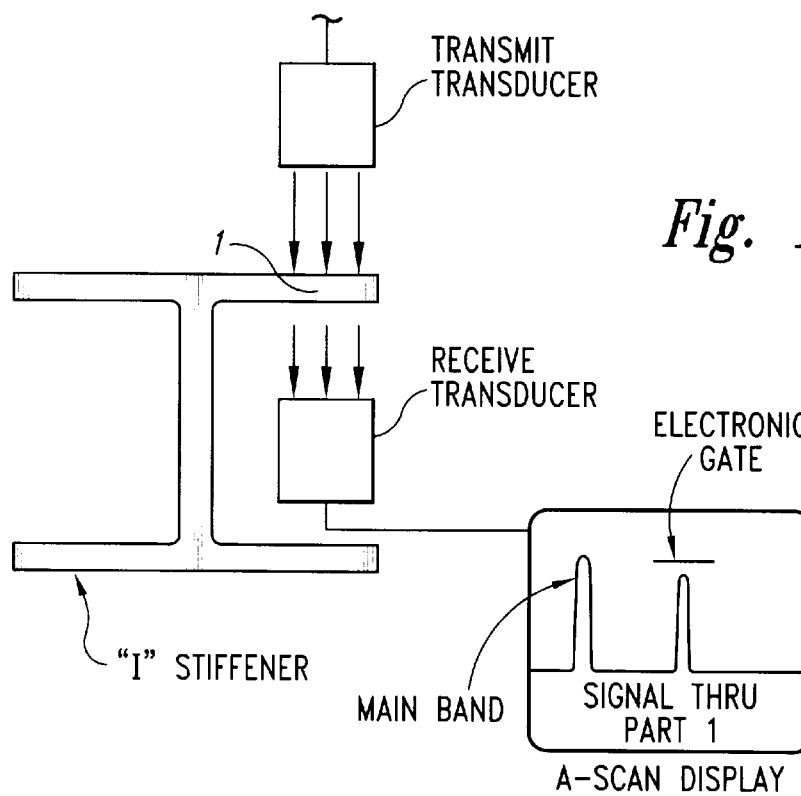
Figure 13:
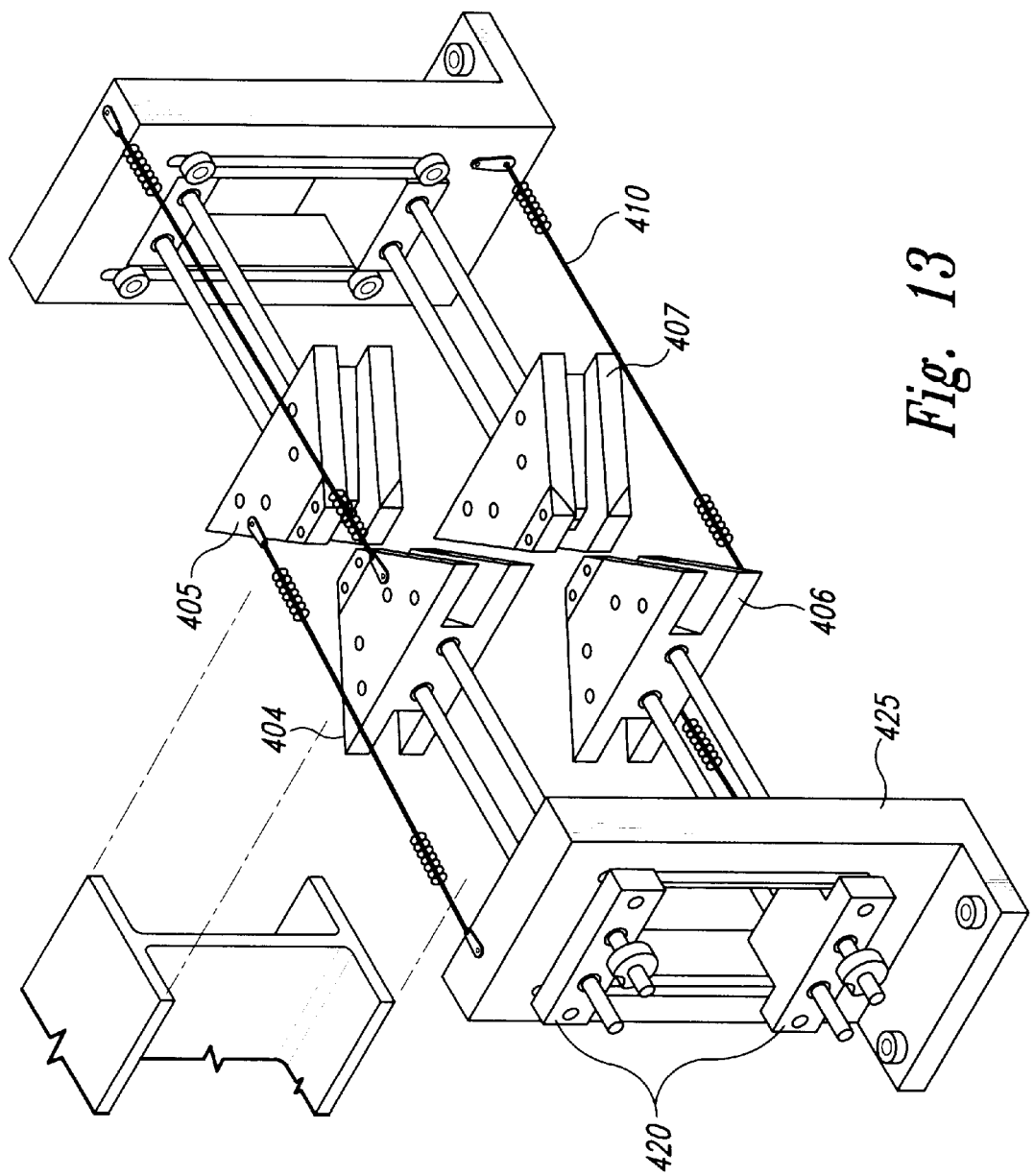
Figure 14:
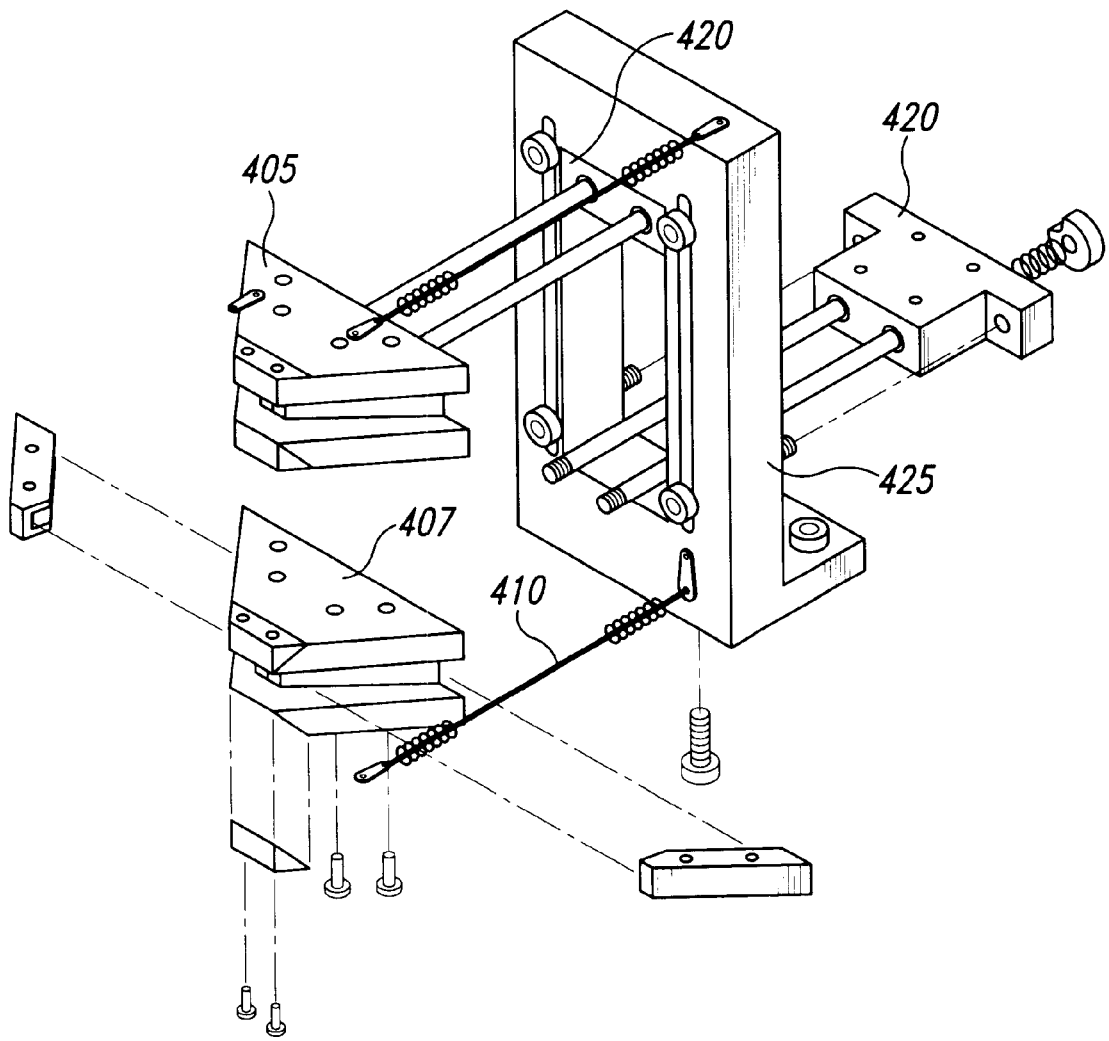
Figure 18:
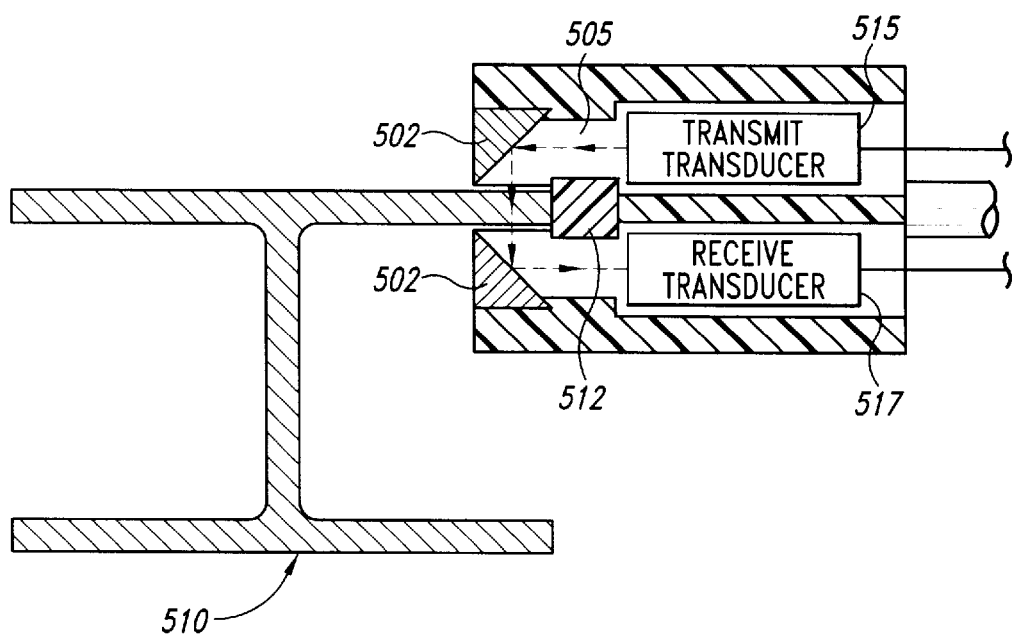

The frontal view of FIG. 7A illustrates the area of inspection coverage;

FIG. 8 is an isometric view of the flange probe;

The frontal view of FIG. 8A illustrates the area of inspection coverage;

FIG. 9 is an isometric view of the web probe;

The frontal view of FIG. 9A illustrates the area of inspection coverage;

FIG. 10 is an isometric view of the cap radius probe;

The frontal view of FIG. 10A illustrates the area of inspection coverage;

FIG. 11 is an isometric view of the flange radius probe;

The frontal view of FIG. 11A illustrates the area of inspection coverage;

FIG. 12 shows positioning of the edge probe transmit and receive transducers relative to the "I" stiffener and ultrasonic signal generated by the edge;

FIG. 12A is illustrative of the positioning of both transmit and receive transducers precisely along the edge;

FIG. 13 is an isometric view of the four edge probes;

FIG. 14 is an isometric view, with parts exploded in relative assembly position of one side of probe;

FIGS. 15, 16 and 17 are pictorial representations sequentially showing the stringer passing through the edge probe; and FIG. 18 is a vertical section showing the use of stainless steel reflectors to redirect the sound beam.

DESCRIPTION OF THE PREFERRED EMBODIMENT

Ultrasonic inspection probes are known in the composite or laminated structure art; e.g., such a probe is described in a U.S. Pat. No. 4,848,159 entitled "Ultrasonic Inspection Probe For Laminated Structures," by Kennedy, et al., assigned to The Boeing Company. The details of probe shoes, including the ultrasonic transducers, the internal conduits, and the biasing spring assemblies shown in U.S. Pat. No. 4,848,159 may be referred to and are incorporated herein by reference.

Figure 1:
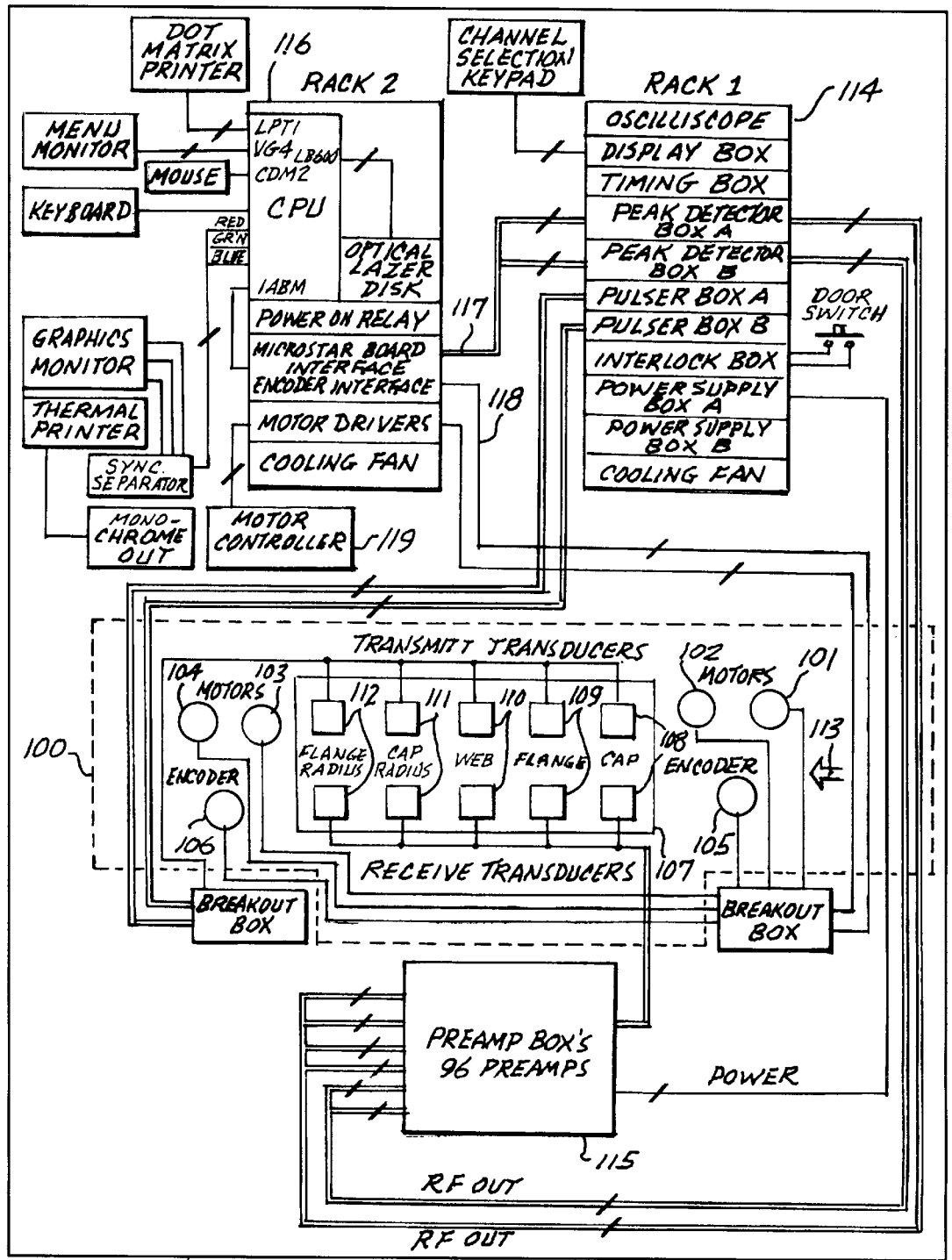
FIG. 1 is a block diagram of the feedthrough "I" stiffener inspection system which includes the motor/encoder system, data acquisition system, and ultrasonic system.

Turning now to FIG. 1, there is illustrated a block diagram of a feedthrough stiffener inspection system (FSIS) 100 in accordance with a preferred embodiment of the present invention. The feedthrough stiffener inspection system includes: two fore motor assemblies 101 and 102; two aft motor assemblies 103 and 104; a fore encoder assembly 105; an aft encoder assembly 106; an immersion tank 107; a cap probe assembly 108; an edge probe assembly 208; a flange probe assembly 109; a web probe assembly 110; a cap radius probe assembly 111; and a flange radius probe assembly 112.

The fore motor assemblies, 101 and 102, and the aft motor assemblies, 103 and 104, operate cooperatively to move the stiffener through immersion tank 107. The stiffener direction is indicated by double arrow 113. Ultrasonic electronics 114 and preamp electronics 115 transmit and receive the ultrasonic signals. Data acquisition system 116 receives and analyzes the encoded position information on line 118 and the ultrasonic signal information on line 117 information on line 118 and the ultrasonic signal information on line 117 to determine the presence, position, and size of flaws in the part under inspection. Controller 119 controls the fore and aft motor drives.

Figure 2A:
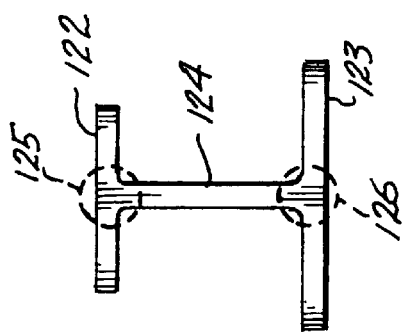
FIG. 2A is a cross-sectional view of the "I" stiffener.
Figure 2:
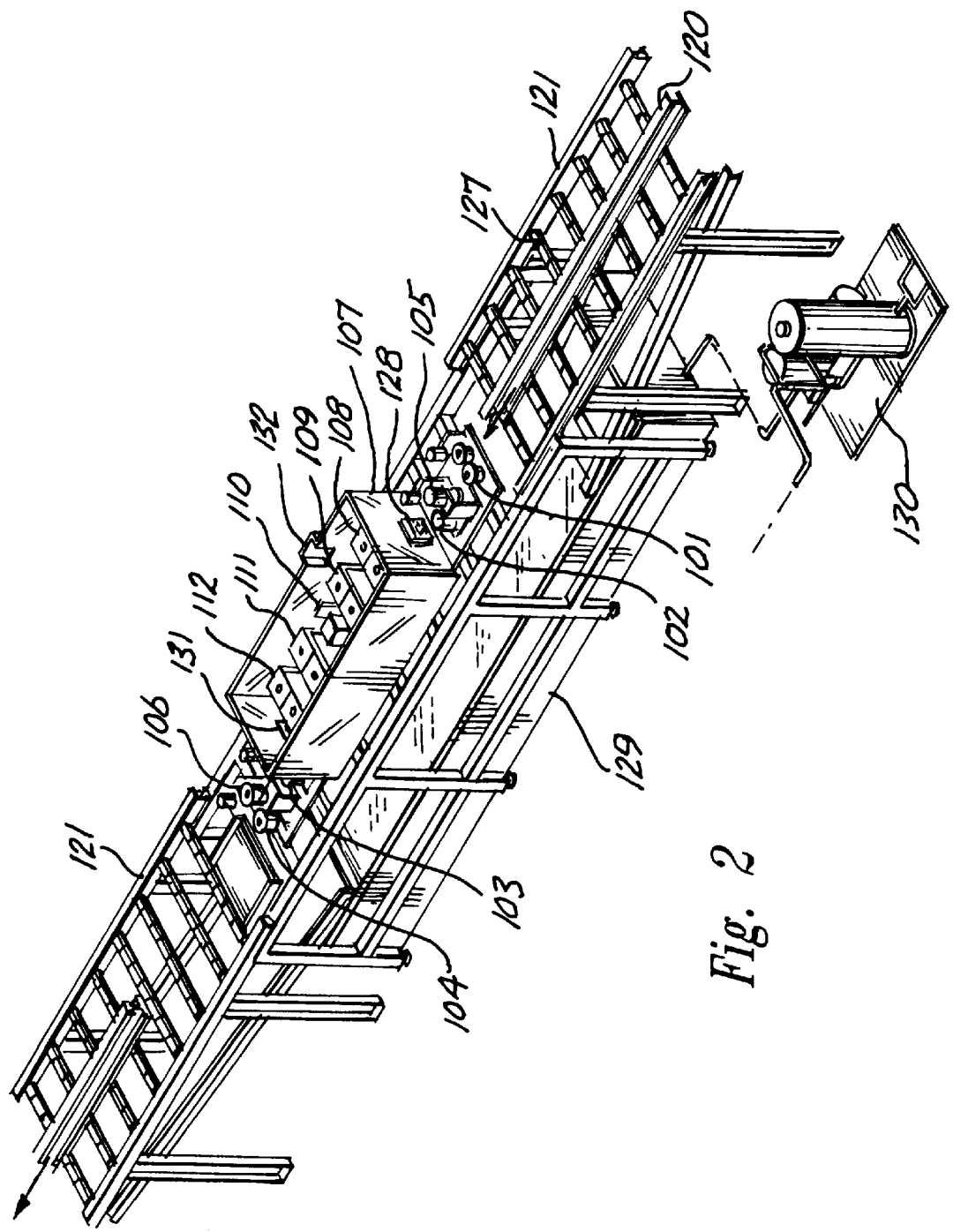
FIG. 2 is a simplified isometric view of the presently preferred embodiment of the feedthrough stiffener inspection system.

FIG. 2 is an isometric view of a preferred embodiment of the present ultrasonic inspection system for laminated stiffeners. A stiffener 120 is resting on the conveyor tables 121 which are both fore and aft of the immersion tank 107. There are a total of six conveyors. The individual rollers 127 are 4 inches long and rotate independently of each other. The "I" stiffener 120 of FIG. 2 has a cap 108, a flange 109, an edge 208, a web 110, a cap radius 111, and a flange radius 112. Stiffener 120 is engaged into motor drive 101 which then begins pulling action. Stiffener 120 then comes in contact with fore encoder 105 which provides the position signals to data acquisition system 116. Engagement with the second fore motor drive 102 forces stiffener 120 to become aligned with the inspection system., Stiffener 120 enters the immersion tank 107 through fore window 128 shaped like the stiffener 120. Window 128 serves two purposes: to further align the stiffener 120, and for reducing the loss of water in immersion tank 107. The water exiting the immersion tank 107 is collected in stainless steel collection tank 129. The water is recirculated by recirculation system 130. The overflow water runs down trough 132 to minimize introduction of air into the water. Air attenuates the ultrasonic signal, thereby producing false readings.

Six probes are required to inspect the entire cross-section of stiffener 120. The five probes are cap 122, flange 123, web 124, cap radius 125, and flange radius 126. Each probe is composed of several shoes that are held together by bearings, rods, and springs. A shoe is a collection of transducers mounted in a machined plexiglass block. Each shoe can hold up to 16 transducers. Each pair of transducers covers an inspection width of 0.125 inch. With the exception of web probe 124, the shape of the ultrasonic probe fits the shape of the part surface, ensuring that there is a stable equilibrium position when the probes are pressed against the part. An edge 208 is also utilized for production inspection. Probe 208 is necessary because of visible delaminations along the edges of the stiffener not detected by either the cap or flange probes. Normally these delaminations are not wide but are tight and therefore not visible with the eye. The ultrasonic signal generated by the edge is shown in FIG. 12. A high voltage electrical spike is sent to the transmit transducer of edge probe 208 generating in FIG. 12, if the transducer was positioned so that the ultrasonic beam were half on the stiffener, the resulting A-scan display (appearing on oscilloscope 114 of FIG. 1) will show the signal through the part (1) and through the water (2). The time between the signals is too small for the electronic gate to differentiate. Therefore, the signal through the water is the only signal detected.

The stiffener exits the aft window 131 which is the same as fore window 128. Stiffener 120 engages first aft motor 103, the aft encoder 106, and the second aft motor 104. A maximum of four motors are pushing/pulling the stiffener through the inspection system. When fore encoder 105 and aft encoder 106 are engaged on the stiffener 120, position information is being generated by fore encoder 105. As the stiffener 120 disengages from fore encoder 105 and stops rotating, aft encoder 106 is activated and starts generating position information. Conveyor table 121 supports the stiffener 120 as it exits the inspection system.

Figure 3:
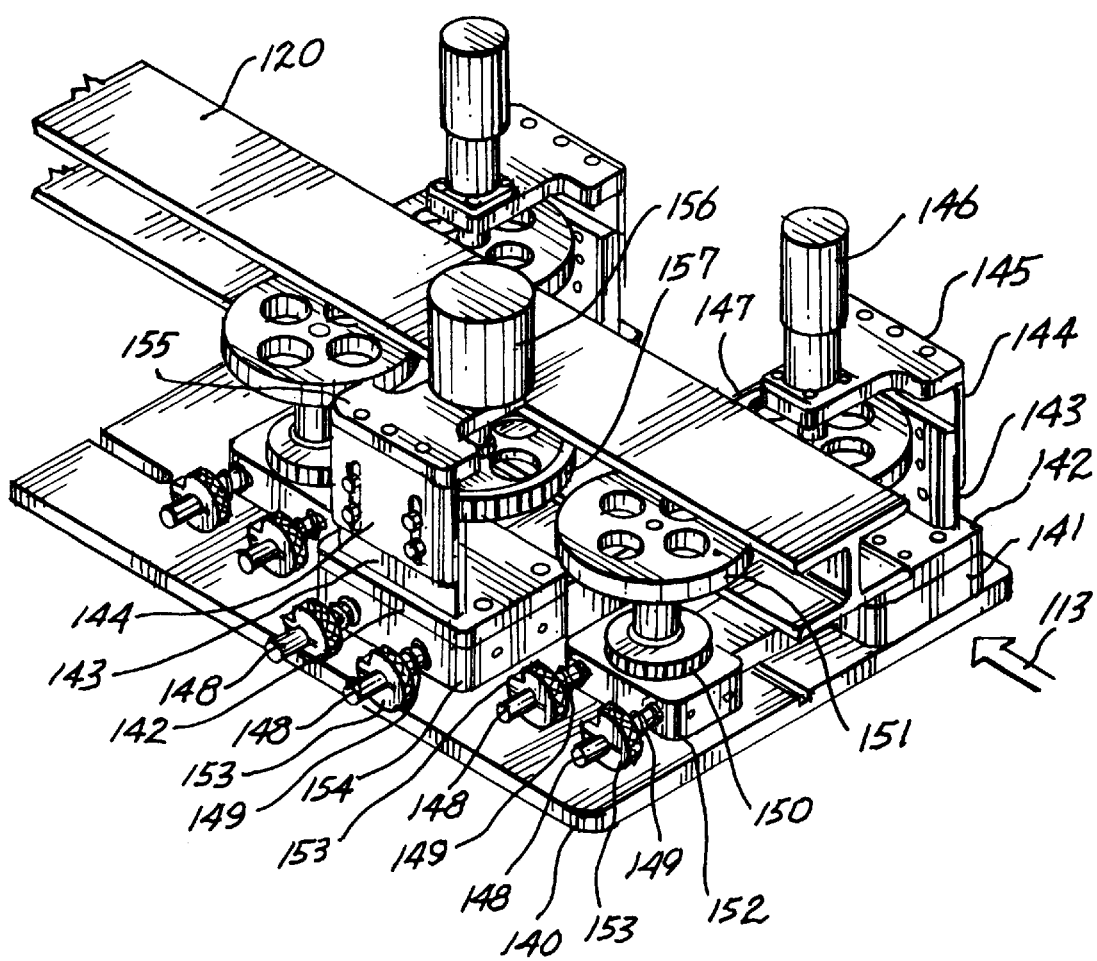
FIG. 3 is an exploded isometric view of the motor/encoder assembly with stiffener.

FIG. 3 is an isometric view of the present motor/encoder assembly. Stiffener direction is shown by double arrow 113. The four motor assemblies are identical. The motor assemblies are attached to a stainless steel base plate. Each motor assembly consists of the following hardware: a fixed mountbase 141; an adjustable mountbase 142; an inside fixed upright 143; an outside adjustable upright 144; a motor mount 145; a motor 146; a grooved drive wheel 147; two shafts 148; two springs 149; a boss 150; a pressure wheel 151; a sliding boss mount 152; and, two split hub clamps 153.

Discussion of motor assembly

Fixed mountbase 141 is attached and keyed to baseplate 140. Inside fixed upright 143 is attached to adjustable mountbase 142 which is attached to fixed mountbase 141. Outside adjustable upright 144 is attached to inside fixed upright 143. Outside adjustable upright 144 can be adjusted vertically for maximum contact against stiffener 120, more specifically, web 124. Grooved drive wheel 147 is attached to motor 146 and this assembly is mounted on motor mount 145. The motor mount is attached to outside adjustable upright 144. Drive wheels 147 are grooved to provide maximum traction against wet stiffener 120. Attached to fixed mountbase 141 are two shafts 148. A pressure wheel assembly opposing the motor assembly provides the pinch force necessary to force stiffener 120 through the inspection system. Attach to shafts 148 is sliding boss mount 152. Boss 151 is attached to sliding boss mount 152. Pressure wheel 150 is attached to a shaft and slides into boss 151. Spring 149 and split hub clamp 153 provide the pinch pressure.

Discussion of encoder assembly

A similar arrangement of mounting to baseplate 140 is employed in the encoder assembly. There is a fixed mountbase 141 and two shafts 148 which extend horizontally for a sliding encoder mountbase 154. Adjustable mountbase 142 is attached to sliding encoder mountbase 154. Inside fixed upright 143 is attached to adjustable mountbase 142. Outside adjustable upright 144 allows encoder 156 and encoder wheel 157 to be adjusted vertically for proper position on stiffener 120, more specifically, web 124. Encoder wheel 157 is attached to encoder top mount 155 which is attached to the outside adjustable upright 144. Spring 149 provides the necessary pressure against web 124 to rotate encoder wheel 157 for generating position information.

FIG. 4 illustrates the window assembly which includes the following: a window guide 161; a rubber seal 162; and a window 163. The direction of the stiffener 120 is depicted by arrow 160. Rubber seal 162 is sandwiched between window 163 and window guide 161. The window assembly is attached to immersion tank 107.

FIG. 5 is a side view of the stiffener just before entering immersion tank 107. Window guide 161 and window guide 163 are slotted to the shape of stiffener 120 cross-section. Rubber seal 162 contains a slit the shape of stiffener 120. The width of the slit on rubber seal 162 is very small, therefore reducing the loss of water through the opening.

FIG. 6 is a side view of stiffener 120 in immersion tank 107. Window guide 161 opening contains a 30-degree angle around the entire inside and outside edge. This provides for some misalignment of the stiffener. As stiffener 120 enters immersion tank 107, the rubber seal comes in contact with stiffener 120. The interaction between rubber seal 162 and stiffener 120 reduces the loss of water through the opening.

Discussion of probe in the immersion tank

FIGS. 7 through 11 represent the probes in the immersion tank. FIG. 7 is an isometric view of a cap probe and stiffener with a frontal view shown in FIG. 7A and area inspected by the cap probe denoted by numeral 201.

FIG. 8 is an isometric view of a flange probe and stiffener with a frontal view shown in FIG. 8A and area inspected by the flange probe denoted by numeral 203.

FIG. 9 is an isometric view of a web probe and stiffener with a frontal view shown in FIG. 9B and area inspected by the web probe denoted by numeral 205.

FIG. 10 is an isometric view of a cap radius probe and stiffener with a frontal view shown in FIG. 10B and area inspected by the cap radius probe denoted by numeral 207.

FIG. 11 is an isometric view of a flange radius probe and stiffener with a frontal view shown in FIG. 11B and area inspected by the flange radius probe denoted by numeral 209.

FIG. 12 shows edge probe 208 location and the aforementioned A-scan display.

The aforementioned five probes are required to inspect the entire cross-section of the stiffener. The five probes are cap, flange, web, cap radius, and flange radius. Edge probe 208 herein before discussed is required to complete production inspection. Each ultrasonic probe is composed of several shoes that are held together by bearings, rods, and springs. A shoe is a collection of transducers mounted in a plexiglass block. Each shoe can hold up to 16 transducers. Each through transmission ultrasonic channel covers an inspection width of 0.125". With the exception of the web probe, the shape of the ultrasonic probe fits the shape of the part surface, thereby ensuring that there is a stable equilibrium position when probes are pressed against the part.

The probes (except the web probe) are attached to a positioner. The positioner has vertical and horizontal adjustments to center the probe for the oncoming stiffener. The positioner allows for the probe to move vertically or horizontally during the inspection. The positioner for each probe is identical and is attached to the bottom of the immersion tank.

The cap and flange probes are identical in design and inspect the cap and flange, respectively. Each probe consists of a pair of vertically opposed shoes. Each pair of vertically opposed shoes contains 16 through transmission ultrasonic channels for a total of 32 channels. The probe is designed to maintain a constant distance from the inspection surface. The maximum inspectable cap width is 4".

The web probe consists of a pair of horizontally opposed shoes. The probe is designed to have a total of 16 channels. The shoes are mounted a fixed distance of 2 inches from the stiffener centerline and do not contact the part. The maximum inspectable web height is 2 inches.

The cap radius and flange radius probe inspect the cap radius and flange radius. Each probe consists of a pair of vertically opposed shoes containing 7 through-transmission ultrasonic channels.

In an exemplary embodiment the system comprises:

|  |  | Transducers |
|---|---|---|
| Cap Probe | = | 64 |
| Flange Probe | = | 64 |
| Wet Probe | = | 32 |
| Cap Radius Probe | = | 8 |
| Flange Radius Probe |  | 8 |
| Edge Probe | = | 8 |
|  |  | 184 Transducers |

FIG. 12 hereinbefore discussed was illustrative of the effect of the ultrasonic signal while the following discussion relating to FIGS. 12A through 18 are believed helpful in demonstrating the purpose of the edge probe in the present ultrasonic inspection system.

The ultrasonic signal generated by the edge is shown in FIG. 12. A high voltage electrical spike is sent to the transmit transducer generating an ultrasonic signal (normally called the main bang). If the transducer was positioned so that the ultrasonic beam was half on the edge, the resulting A-scan trace will show the signal through the part and through the water. The time between the signals is too small for the electronic gate to differentiate. The electronic gate detects only the largest signal and that is the signal through the water. As shown in FIG. 12A, if both the transmit and receive transducers were located precisely along the edge, a single ultrasonic signal would be displayed. That is the signal through the edge.

FIG. 13 shows the relative positioning of the four edge probes 404, 405, 406 and 407 spring mounted with adjustable means 420 on stationery base 425 while FIG. 14 is an isometric exploded view showing in more detail one side of the probe assembly of FIG. 13. FIGS. 15, 16 and 17 are pictorial representations showing sequentially the stringer passing through the edge probe assembly.

FIG. 18 is a vertical section showing stainless steel reflectors 502 for redirecting sound beam 505 into the edge of stringer 510. Locator strip 512 enables positioning of transmit transducer 515 and receive transducer 517 precisely along the edge thereby further enabling, as hereinbefore discussed, the display of a single ultrasonic signal.

What is claimed is:

1. An ultrasonic inspection system for inspecting an aircraft stiffener comprising an immersion system including in combination:

motor drive wheels;

a fore and aft motor drive assembly;

said fore and aft motor drive assemblies operating synchronously;

a spring loaded platform;

said fore and aft motor drive assemblies mounted on said spring-loaded platform for pushing said fore and aft motor drive assemblies against the aircraft stiffener;

a non-movable fixed drive wheel disposed opposite said motor drive wheels; the interaction of said motor drive wheels providing translational movement of the stiffener through said immersion system;

said immersion system including an immersion tank having an edge probe within said immersion tank for inspecting the edge of said aircraft stiffener;

fore and aft position encoder assemblies operating synchronously;

said fore position encoder assembly actuated as an aircraft stringer moves through said immersion system; and said aft position encoder assembly activated when said aircraft stringer disengages from said fore position encoder assembly until said aircraft stringer disengages from said aft position encoder assembly.

* * * * *